United States Patent [19]

Pettine

[11] Patent Number: 4,955,370
[45] Date of Patent: Sep. 11, 1990

[54] ACHILLES TENDON REHABILITATION BRACE AND METHOD FOR ITS MANUFACTURE

[76] Inventor: Kenneth A. Pettine, 201 Threadneedle Rd., East, Augusta, Ga. 30907

[21] Appl. No.: 332,895

[22] Filed: Apr. 4, 1989

[51] Int. Cl.⁵ ................................................ A61F 3/00
[52] U.S. Cl. ................................. 128/80 E; 128/80 H
[58] Field of Search ..................... 128/80 H, 166, 83.5, 128/84 R, 80 R, 80 E, 80 F

[56] References Cited

U.S. PATENT DOCUMENTS

| | | | |
|---|---|---|---|
| 130,639 | 8/1872 | Howe | 128/166 |
| 1,549,382 | 8/1925 | Riddell . | |
| 2,107,095 | 2/1938 | Wagner | 128/80 F |
| 2,477,591 | 8/1949 | Follis | 128/80 H |
| 2,516,872 | 8/1950 | Hauser et al. | 128/80 H |
| 2,536,454 | 1/1951 | McIntyre | 128/80 E |
| 3,064,644 | 11/1962 | Patterson . | |
| 3,732,861 | 5/1973 | Lehneis | 128/80 E |
| 3,804,085 | 4/1974 | Eshius et al. | 128/80 E |
| 3,805,773 | 4/1974 | Sichau | 128/80 E |
| 4,392,487 | 7/1983 | Selner et al. | 128/80 H |
| 4,566,447 | 1/1986 | Deis | 128/80 E |
| 4,646,726 | 3/1987 | Westin et al. | 128/80 H |
| 4,771,768 | 9/1988 | Crispin | 128/88 |
| 4,834,078 | 5/1989 | Biedermann | 128/80 H |

FOREIGN PATENT DOCUMENTS

| | | | |
|---|---|---|---|
| 888866 | 12/1943 | France | 128/80 E |
| 593057 | 11/1977 | Switzerland | 128/80 E |
| 325970 | 3/1972 | U.S.S.R. . | |

Primary Examiner—Edgar S. Burr
Assistant Examiner—Huong Q. Pham

[57] ABSTRACT

An Achilles tendon rehabilitation brace for protecting motion that may be imposed on a repaired Achilles tendon following surgical anastomosis consisting of a member receiving shoewear to be received and secured upon a rugged slip resistant sole, side arms having upper and lower extremities vertically disposed proximate an ankle portion, the lower extremity securely attached to the sole, the upper extremity pivotally securely attached to a lower terminus corresponding medial and lateral uprights, an upper terminus of the medial and lateral uprights coupled to flexible, spring resilient strap engaging upon a calf area of one's leg, toe arm member having upper and lower extremities generally vertically disposed proximate an instep area of the toe, the lower extremity securely attached to the sole, the upper extremity pivotally securely attached to a lower terminus of an extensible link, an upper terminous of the link coupled to an instep side portion of the strap, and a tension adjustable spring member included within the link to urge and extend one's ankle into plantar flexion.

8 Claims, 1 Drawing Sheet

ACHILLES TENDON REHABILITATION BRACE AND METHOD FOR ITS MANUFACTURE

BACKGROUND OF THE INVENTION

1. Field of the Invention

The invention relates to an improved Achilles tendon rehabilitation brace and the method for its manufacture, and more particularly the invention is directed to an Achilles tendon rehabilitation brace for protecting motion that may be imposed on a repaired Achilles tendon following surgical anastomosis consisting of a member for receiving shoewear to be received and secured upon a rugged slip resistant sole, side arms having upper and lower extremities vertically disposed proximate an ankle portion, the lower extremity being securely attached to the sole, the upper extremity pivotally and securely attached to a lower terminus corresponding medial and lateral uprights, an upper terminus of the medial and lateral uprights coupled to flexible, spring resilient strap engaging upon a calf area of one's leg, a toe member having upper and lower extremities generally vertically disposed proximate an instep area of the toe, the lower extremity thereof securely attached to the sole, the upper extremity pivotally and securely attached to a lower terminus of an extensible link, an upper terminous of the link coupled to an instep side portion of the strap, and a tension adjustable spring member included within the link to urge and extend one's ankle into plantar flexion.

The invention relates further to an Achilles tendon rehabilitation device providing for a shoe mounted, pivoted ankle brace with a leg support that is provided with a tension adjustable spring being toe and leg mounted, and is used to push the ankle into plantar flexion position when notused otherwise, and also relates to the method of of its construction thereof as more particularly described herein.

2. Description of the Prior Art

Various prior art braces useful in rehabilitation of Achilles tendons and the like, as well as apparatus and method of their construction in general, are found to be known, and exemplary of the prior art are the following:

Howe: 130,639
Riddell: 1,549,382
Patterson: 3,064,644
Crispin: 4,771,768
USSR Patent: 325,970(1970)

Patterson shows a spring member used to raise the toe to the shoe. The USSR patent shows an orthopedic appliance for an ankle joint; apparently a helical spring cooperates with a spring lever; a brief translation of the USSR abstract states: "back deflection of the foot and smooth bending of the soles of the foot are made possible with vertical axis of the clamper offset in relation to the vertical passing through the ankle joint pivot in the direction of the heel. The stud of the pivot carries coaxial turns of the spring which forms elastic levers attached to strap by a clip. The vertical axis of clamper 6 is offset from the axis of the stud."

These patents or known prior uses teach and disclose various types of brace devices of sorts and of various manufactures and the like as well as methods of their construction, but none of them whether taken singly or in combination disclose the specific details of the combination of the invention in such a way as to bear upon the claims of the present invention.

SUMMARY OF THE INVENTION

An object, advantage and feature of the invention is to provide a novel Achilles tendon rehabilitation brace that will provide more complete freedom of action about the ankle during healing processes.

Another object of the invention is directed further to an Achilles tendon rehabilitation brace and the method of its construction thereof to produce a brace so that the person of the wearer can readily manipulate the brace without the aid of others.

Also an object of the invention is to provide a simple and direct method for the improved construction of an Achilles tendon rehabilitation brace that overcomes various objections that are found in prior devices.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWING

The drawing shows a perspective view of an Achilles tendon rehabilitation brace and illustrating a typical installation of the brace according to a preferred embodiment and best mode of the present invention.

DESCRIPTION OF A PREFERRED EMBODIMENT OF THE INVENTION

Figure 1:
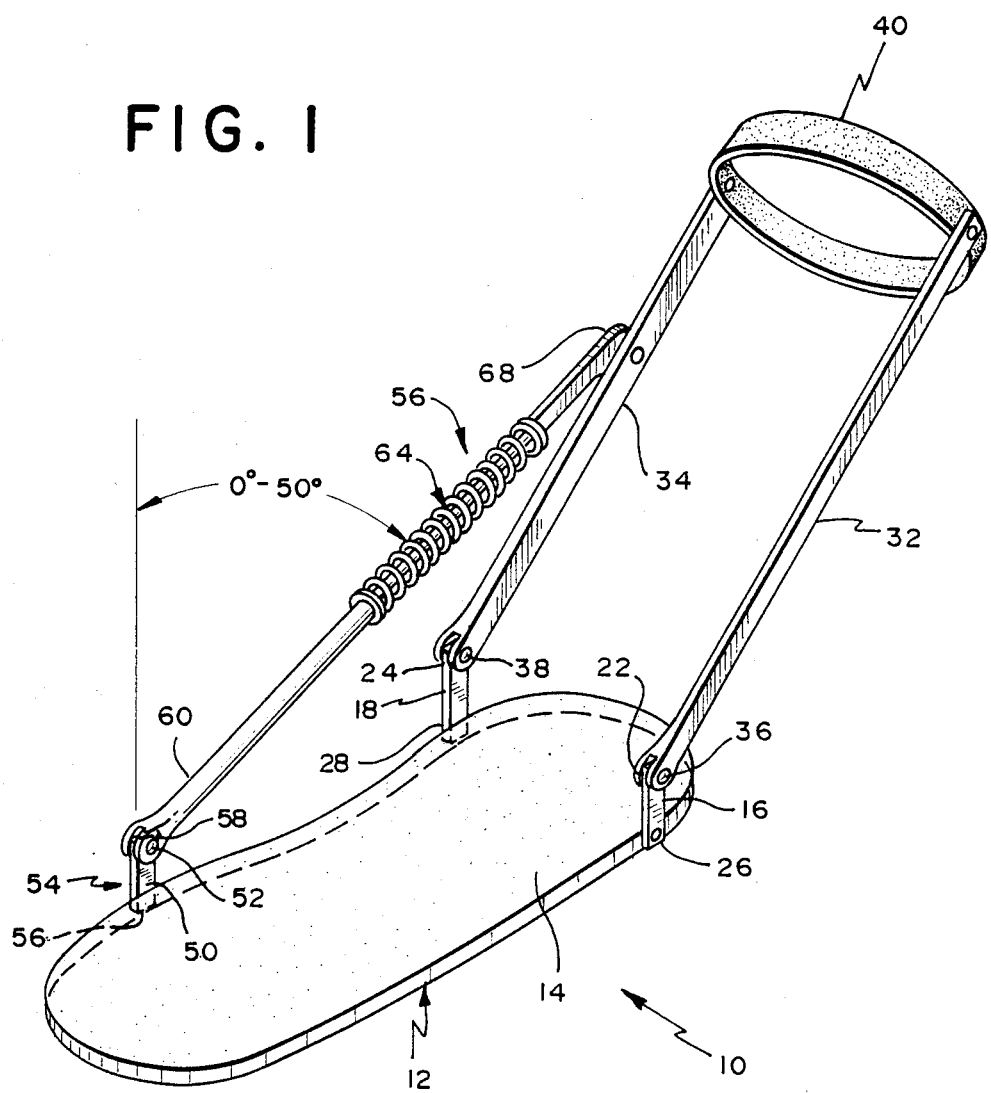

Referring now to the drawing there is shown an Achilles tendon rehabilitaion brace 10 and including a member 12 for receiving shoewear (not shown) to be received and secured upon a rugged slip resistant sole 14 with side arms 16, 18 having upper extremities 22, 24 and lower extremities 26, 28 disposed generally vertically and proximate an ankle portion (not shown), the lower extremities 26, 28 are securely attached to the sole 14, and the upper extremities 22, 24 are pivotally and securely attached to a lower terminus corresponding medial and lateral uprights 32, 34 by respective pivots 36, 38.

Each of the upper termini of the medial and lateral uprights 32, 34 are coupled to a flexible, spring resilient strap 40 for engaging upon a calf area of one's leg (not shown).

A toe member 44 has an upper extreme end 58 connected a pin 52 to the flexible, spring resilient strap 40 by an extensible link assembly 60, 64, which includes an extensible link 60 and an adjustable spring member 64 that may be disposed within a chamber or like member for the spring member to provide its tension and to push a foot into plantar flexion from a neutral position, wherein the link means distends the side arms and lateral uprights through an arc about 0°-50° and a lower extreme end 50 is generally vertically disposed proximate an instep area side 54 of the toe of the shoewear. The lower extreme end 50 is securely attached to the sole 14 by a pivot or securement to the extensible link assembly 60, 64 and the upper extreme end 58 is pivotally and securely attached to a lower terminus of the extensible link assembly 60, 64.

An upper terminous of the link 60 is coupled to an instep side portion of the strap 40, and a tension adjustable spring member 64 is included within the link assembly 60, 64 to urge and extend one's ankle into plantar flexion relation.

The apparatus of the Achilles tendon rehabilitation brace 10 of the invention may be so constructed and arranged in its component parts that it may be assembled as a kit or in kit form.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters Patent is:

1. An Achilles tendon rehabilitation brace attachable to a shoewear for protecting motion that may be imposed on a repaired Achilles tendon following surgical anastomosis comprising a rugged slip resistant sole means, medial and lateral uprights, a flexible spring resilient strap, an extensible link means, means for shoewear to be received and secured upon an edge of the rugged slip resistant sole means, side arms having upper and lower extremities vertically disposed proximate an ankle of the user, the lower extremities being securely attached to the sole means, the upper extremities being pivotally securely attached to a lower terminus of the corrsponding medial and lateral uprights, the upper terminus of the medial and lateral uprights being coupled to said flexible, spring resilient strap for engaging upon a calf area of a user's leg, toe arm means having upper and lower extreme ends generally vertically disposed proximate the instep side of the shoewear, the lower extreme end being securely attached to the sole means, the upper extreme end being pivotally and securely attached to a lower terminus of said extensible link means, an upper terminus of the link means being coupled to an instep side of the strap, and tension adjustable spring means included within the link means to urge and extend a user's ankle into plantar flexion.

2. The apparatus of claim 1 wherein the shoewear is a generally conventional type of shoe.

3. The apparatus of claim 1 wherein the shoewear is an athletic shoe.

4. The apparatus of claim 1 wherein the link means distends the side arms and lateral uprights through an arc of about 0° to 50°.

5. Method of making an Achilles tendon rehabilitation brace for protecting motion that may be imposed on a repaired Achilles tendon following surgical anastomosis comprising the steps of providing a rugged slip resistant sole, securing a shoewear element upon the rugged slip resistant sole, providing side arms having upper and lower extreme ends vertically disposed proximate the ankle, of a user, securing the lower extreme ends of said side arms to the sole, providing medial and lateral uprights, pivotally securing the upper extreme ends of said side arms to a lower terminus of the corresponding medial and lateral uprights, connecting an upper terminus of the medial and lateral uprights to a flexible, spring resilient strap for engaging upon a calf area of a user's leg, providing a toe member having upper and lower extreme ends being generally vertically disposed and positioned proximate an instep area of the shoewear, connecting the lower extreme end of said toe member to the sole, attaching the upper extreme end of said toe member pivotally and securely to a lower terminus of an extensible link, connecting an upper terminus of the link to the instep side portion of the strap, and inserting a tension adjusting spring member within the link to urge and extend a user's ankle into plantar flexion.

6. The method of claim 5 wherein the shoewear is a generally conventional type of shoe.

7. The method of claim 5 wherein the shoewear is an athletic shoe.

8. The method of claim 5 wherein the link means distends the side arm and lateral upright through an arc of about 0° to 50°.

* * * * *